United States Patent
VanDyk et al.

(10) Patent No.: US 7,273,842 B1
(45) Date of Patent: Sep. 25, 2007

(54) COLORANTS, DISPERSANTS AND DISPERSIONS CONTAINING POLYMERIC NANOPARTICLES

(75) Inventors: Antony Keith VanDyk, Blue Bell, PA (US); Dennis Paul Lorah, Lansdale, PA (US)

(73) Assignee: Rohm and Haas Company, Philadelphia, PA (US)

( * ) Notice: Subject to any disclaimer, the term of this patent is extended or adjusted under 35 U.S.C. 154(b) by 244 days.

(21) Appl. No.: 10/461,953

(22) Filed: Jun. 13, 2003

Related U.S. Application Data

(60) Provisional application No. 60/414,596, filed on Sep. 30, 2002, provisional application No. 60/389,043, filed on Jun. 14, 2002.

(51) Int. Cl.
*C11D 3/37* (2006.01)
(52) U.S. Cl. ............... 510/475; 510/476; 510/477; 424/484; 523/409; 526/75
(58) Field of Classification Search ............... 510/475, 510/476, 477; 523/409; 424/484; 526/75
See application file for complete search history.

(56) References Cited

U.S. PATENT DOCUMENTS

| | | | | |
|---|---|---|---|---|
| 4,560,714 | A | 12/1985 | Gajria et al. | 523/409 |
| 4,588,639 | A * | 5/1986 | Ozono | 428/402.22 |
| 5,064,923 | A * | 11/1991 | Kashihara et al. | 526/265 |
| 5,212,273 | A | 5/1993 | Das et al. | 526/323.1 |
| 5,597,557 | A * | 1/1997 | Kumar et al. | 424/70.17 |
| 5,863,996 | A | 1/1999 | Graham | 526/216 |
| 6,207,195 | B1 * | 3/2001 | Walsh et al. | 424/489 |
| 6,214,467 | B1 | 4/2001 | Edwards et al. | 428/407 |
| 6,268,222 | B1 | 7/2001 | Chandler et al. | 436/523 |
| 6,329,446 | B1 | 12/2001 | Sacripante et al. | 523/161 |
| 6,333,051 | B1 * | 12/2001 | Kabanov et al. | 424/484 |
| 2002/0065208 | A1 | 5/2002 | Aubay et al. | 510/475 |
| 2003/0055178 | A1 * | 3/2003 | Gore et al. | 525/242 |
| 2003/0181540 | A1 * | 9/2003 | Quellet et al. | 523/102 |
| 2003/0232914 | A1 * | 12/2003 | Devonport et al. | 524/501 |

FOREIGN PATENT DOCUMENTS

| | | |
|---|---|---|
| DE | 196 51 689 A1 | 6/1998 |
| EP | 1 245 644 A2 | 10/2002 |
| EP | 1371685 A2 * | 12/2003 |
| WO | WO 93/00376 | 1/1993 |
| WO | WO 93/24534 | 12/1993 |
| WO | WO 98/33865 | 8/1998 |
| WO | WO 99/01522 | 1/1999 |
| WO | WO 00/59951 | 10/2000 |
| WO | WO 01/43859 | 6/2001 |
| WO | WO 01/90226 | 11/2001 |
| WO | WO 02/066483 A1 | 8/2002 |

OTHER PUBLICATIONS

U.S. Appl. No. 10/461,956, filed Jun. 13, 2003, Ghosh et al.
U.S. Appl. No. 10/461,958, filed Jun. 13, 2003, Bowe.
U.S. Appl. No. 10/461,964, filed Jun. 13, 2003, Lauer et al.
U.S. Appl. No. 10/461,963, filed Jun. 13, 2003, Even et al.
U.S. Appl. No. 10/461,959, filed Jun. 13, 2003, Lauer et al.
U.S. Appl. No. 10/461,949, filed Jun. 13, 2003, Lofton et al.
U.S. Appl. No. 10/461,954, filed Jun. 13, 2003, Amick et al.
U.S. Appl. No. 10/461,955, filed Jun. 13, 2003, Kauffman et al.
U.S. Appl. No. 10/461,952, filed Jun. 13, 2003, Devonport et al.
U.S. Appl. No. 10/462,111, filed Jun. 13, 2003, Cruz.
U.S. Appl. No. 10/461,948, filed Jun. 13, 2003, Lorah.
U.S. Appl. No. 10/462,110, filed Jun. 13, 2003, Devonport et al.
U.S. Appl. No. 10/461,965, filed Jun. 13, 2003, Lester et al.
U.S. Appl. No. 10/461,971, filed Jun. 13, 2003, Daly et al.
U.S. Appl. No. 10/097,256, filed Mar. 15, 2002, Beckley et al.
U.S. Appl. No. 10/452,175, filed Jun. 2, 2003, Amick et al.
Dieter Horn and Jens Rieger, "Organic Nanoparticles in the Aqueous Phase—Theory, Experiment, and Use", Agnew, Chem. Int. Ed. 2001, 40, pp. 4330-4361.

* cited by examiner

*Primary Examiner*—David W. Wu
*Assistant Examiner*—Henry S. Hu

(57) ABSTRACT

Colorants, dispersants, and dispersions are provided which include PNPs having a mean diameter in the range of from 1 to 50 nanometers, an acid value in the range of from 0 to 700 mg KOH/g PNP solids, an amine value in the range of from 0 to 250, a hydroxyl number in the range of from 0 to 250 mg KOH/g PNP solids, and containing at least 2 wt % of a polarizable group. Also provided are methods for preparing colorants, dispersants, and dispersions, which include PNPs.

3 Claims, No Drawings

COLORANTS, DISPERSANTS AND DISPERSIONS CONTAINING POLYMERIC NANOPARTICLES

CROSS REFERENCE TO RELATED PATENT APPLICATIONS

This is a non-provisional application of prior pending U.S. provisional application Ser. No. 60/389,043 filed Jun. 14, 2002 and 60/414,596 filed Sep. 30, 2002.

The present invention relates to colorants, dispersants, and dispersions all of which include crosslinked polymeric nanoparticles (PNPs). The invention also relates to methods for preparing such PNP-containing colorants, dispersants, and dispersions.

Many types of colorants, such as organic or inorganic pigment particles and dyes are dispersible in liquids. Like many particle dispersions, colorant dispersions tend to be inherently unstable. Primarily, this is because the colorants themselves, usually in the form of organic or inorganic pigments, are often provided as large (e.g., greater than 100 micron) agglomerates of aggregated colorant particles. The natural tendency of pigment particles is to aggregate. To reverse the initial state of agglomeration, many colorants require an extensive input of energy, for example, through grinding and milling, and require the use of specific dispersants to prepare dispersions of smaller colorant particles, such as primary pigment particles. Typically, complete dispersion is not achieved, and instead an equilibrium between primary particles and agglomerates is formed. Examples of suitable dispersants are anionic, cationic, and nonionic surfactants and polymeric dispersants. A disadvantage of currently existing dispersants is that they confer a limited depth of charge and steric stabilization to a pigment surface. An additional disadvantage of existing dispersants is that the strength with which the dispersant is adsorbed onto the colorant surface is not sufficient to provide for complete coverage of the entire surface of the pigment particles. The resulting partial coverage of colorant surfaces causes incomplete stabilization of the colorant surface. Additionally, due to the insufficient adsorption strength, large amounts of dispersant remain in solution in the continuous phase. The concentration of the dispersant in the continuous phase decreases upon dilution or mixing with other compositions, such as a paint, thickeners, defoamers, surfactants, solvents and other paint additives. This results in the reduction of dispersant attached to the colorant surface which in turn causes reduced stability of the colorant dispersion, as well as the exposure of the depleted pigment surface to other types of molecules that compete with the dispersant for adsorption onto the colorant surface. The reduced stability of the colorant dispersion leads to flocculation. Additional flocculation occurs upon application of shear to the colorant dispersion of reduced stability, such as during mixing of the colorant particles to form the colorant dispersion, or during application of a composition containing the colorant dispersion, particularly if the application means is by brush or spray. As a result of this flocculation, the color and opacity of the materials incorporating the colorant is uncertain, variable, and extremely difficult to reproduce and control with precision. While the above problems are more apparent with colorants in the form of pigments than with colorants in the form of dyes, many dyes tend to fade on exposure to heat, light, and radiation (poor light fastness). Additionally, many dyes also tend to migrate (i.e., "bleed").

In light of the abovementioned problems, improved colorants, colorant dispersions, and dispersants are desirable.

Others have designed dispersant molecules from monomers, oligomers and macromolecules combined together in a variety of ways. For example, U.S. Pat. No. 4,560,714 discloses carboxylic acids containing water-swellable polymeric microgel particles, the microgel particles being useful for coating stabilization. However, the microgel particles are prepared by emulsion polymerization, and have a particle size of 0.05 to 200 microns (50 to 200,000 nm). U.S. Pat. No. 6,214,467 (the '467 patent) discloses latex polymer-pigment composite particles useful for dispersing $TiO_2$ particles. However the polymer particles of the '467 patent are formed from 0.05 to 20 wt % of at least one terminally unsaturated oligomer having a particular formula.

Applicants have discovered that the aforementioned problems are overcome by including crosslinked polymeric nanoparticles (PNPs) in the compositions of colorants, dispersants, dispersions and inks, where the PNPs have a particular particle diameter, acid value, amine value and hydroxyl number, and contain, as polymerized units, at least one multi-ethylenically unsaturated monomer. In particular, Applicants have discovered that the use of colorants and dispersants incorporating such PNPs enables the formation of high solids, low viscosity colorant dispersions that retain their stability and the integrity of adsorbed dispersant layers upon dilution and upon mixing with a wide variety of compositions.

As used herein, the following abbreviations shall have the following meanings, unless the context clearly indicates otherwise: C=centigrade; ?m=micron; D=Debye; C m=Coulomb meter; UV=ultraviolet; rpm=revolutions per minute; nm=nanometer; J=joules; cc=cubic centimeter; g=gram; wt %=weight percent; L=liter; mL=milliliter; PVC=(Total volume of colorant)/(Total volume of colorant plus total volume of all other nonvolatile ingredients); MIAK=methyl iso-amyl ketone; MIBK=methyl iso-butyl ketone; BA=butyl acrylate; AA=acrylic acid; MAA=methacrylic acid; PS=particle size=mean diameter; PMA=poly(methyl acrylate); CyHMA=cyclohexyl methacrylate; EG=ethylene glycol; DPG=dipropylene glycol; DEA=diethylene glycol ethyl ether acetate; BzA=benzyl acrylate; BzMA=benzyl methacrylate; MAPS=MATS=(trimethoxylsilyl)propyl methacrylate; PETTA=pentaerythritol tetra/triacrylate; PPG4000DMA=polypropyleneglycol 4000 dimethacrylate; OFPMA=octafluoropentyl methacrylate; DPEPA=dipentaerythritol pentaacrylate; TMSMA=trimethylsilyl methacrylate; MOPTSOMS=methacryloxypropylbis(trimethylsiloxy)methylsilane; MOPMDMOS=3-methacryloxypropylmethyldimethoxysilane; TAT=triallyl-1,3,5-triazine-2,4,6-(1H,3H,5H)-trione; IBOMA=isobornyl methacrylate; PGMEA=propyleneglycol monomethylether acetate; PEGMEMA475=poly(ethylene glycol methyl ether) methacrylate Mw=475; and PGDMA=propyleneglycol dimethacrylate.

Unless indicated otherwise, the use of the term "or" herein refers to the inclusive form of "or", e.g., the condition "A or B" is true when at least one of the following is satisfied: A is true; B is true; A and B are both true.

In a first aspect of the present invention, there is provided a colorant composition comprising at least one chromophore and polymeric nanoparticles (PNPs); wherein said PNPs comprise, as polymerized units, at least one multi-ethylenically unsaturated monomer; and wherein said PNPs have a mean diameter in the range of from 1 to 50 nanometers, an acid value in the range of from 0 to 700 mg KOH/g PNP solids, an amine value in the range of from 0 to 250, a hydroxyl number in the range of from 0 to 250 mg KOH/g PNP solids, and contain at least 2% of a polarizable group.

In a second aspect of the present invention, there is provided a dispersion, comprising particles and PNPs, both the particles and PNPs being dispersed in a liquid medium, wherein said PNPs comprise, as polymerized units, at least one multi-ethylenically unsaturated monomer; and wherein said PNPs have a mean diameter in the range of from 1 to 50 nanometers, an acid value in the range of from 0 to 700 mg KOH/g PNP solids, an amine value in the range of from 0 to 250, a hydroxyl number in the range of from 0 to 250 mg KOH/g PNP solids, and contain at least 2% of a polarizable group.

In a third aspect of the present invention, there is provided a dispersant, comprising at least one PNP, wherein said at least one PNP comprises, as polymerized units, at least one multi-ethylenically unsaturated monomer; and wherein said at least one PNP has a mean diameter in the range of from 1 to 50 nanometers, an acid value in the range of from 0 to 250 mg KOH/g PNP solids, an amine value in the range of from 0 to 700, a hydroxyl number in the range of from 0 to 250 mg KOH/g PNP solids, and contain at least 2% of a polarizable group.

In a fourth aspect of the present invention, there is provided a method of providing a colorant comprising: (1) forming PNPs, said PNPs comprising, as polymerized units, at least one multi-ethylenically unsaturated monomer; wherein said PNPs have a mean diameter in the range of from 1 to 50 nanometers, an acid value in the range of from 0 to 700 mg KOH/g PNP solids, an amine value in the range of from 0 to 250, a hydroxyl number in the range of from 0 to 250 mg KOH/g PNP solids, and contain at least 2% of a polarizable group; and (2) attaching at least one chromophore to at least a portion of said PNPs.

In a fifth aspect of the present invention, there is provided a method of providing a dispersant comprising forming PNPs, wherein said PNPs comprise, as polymerized units, at least one multi-ethylenically unsaturated monomer; and wherein said PNPs have a mean diameter in the range of from 1 to 50 nanometers, an acid value in the range of from 0 to 700 mg KOH/g PNP solids, an amine value in the range of from 0 to 250, and a hydroxyl number in the range of from 0 to 250 mg KOH/g PNP solids, and contain at least 2 wt % of a polarizable group.

In a sixth aspect of the present invention, there is provided a method of providing a dispersion comprising: (1) forming PNPs, wherein said PNPs comprise, as polymerized units, at least one multi-ethylenically unsaturated monomer; wherein said PNPs have a mean diameter in the range of from 1 to 50 nanometers, an acid value in the range of from 0 to 700 mg KOH/g PNP solids, an amine value in the range of from 0 to 250, and a hydroxyl number in the range of from 0 to 250 mg KOH/g PNP solids, and contain at least 2 wt % of a polarizable group; and (2) dispersing at least one particle with said PNPs in a liquid medium.

The composition of the present invention relates to a colorant composition which contains at least one chromophore and PNPs. By "colorant" herein is meant a substance that interacts with radiant energy. By "interacts with radiant energy" herein is meant the scattering, altering or generation by a substance of radiant energy, such as for example photons, visible light and heat, sound and acoustic energy, fermions, and electrons. Examples of colorants that are suitable for the present invention include, for example, pigments and dyes. By "pigment" herein is meant a colorant in the form of a particulate organic or inorganic substance. Within the purview of this invention, inorganic particles include, but are not limited to, particulate minerals, clays, ceramics, metals, metal oxides and the like. By "dye" herein is meant a colorant in the form of non-particulate organic or inorganic substance, e.g., a molecule containing a chromophore.

The colorant composition of the present invention contains at least one chromophore. By "chromophore" herein is meant a component which interacts with radiant energy such as by absorption, reflection, flatting, thermochromism, photochromism, dichromism, interference, conductivity, insulation, electroluminescence, chemiluminescence, phosphorescence, or fluorescence. The colorants of this invention are made in the presence of the PNPs, by subsequent treatment or interaction of chromophoric moieties with PNPs, or by subsequent treatment or interaction of pigment with PNPs. In this invention, the chromophoric moieties and the PNPs are attached through covalent forces (e.g., to form PNP-dye or PNP-pigment macromolecules), ionic forces (e.g., to form a PNP-dye or PNP-pigment salt), dispersive forces (e.g., to form PNP-dye or PNP-pigment composites), or combinations of these forces. These solutions are either aqueous, non-aqueous, or a mixture of aqueous and non-aqueous. Accordingly, colorants are provided by reacting, precipitating, adsorbing, agglomerating, or otherwise combining PNPs with pigments or dyes or combinations thereof. The PNPs preferably are functionalized for covalent or ionic bonding to the chromophoric moieties. Various methods of attaching dyes to functionalized vinyl polymers are provided in U.S. Patent Application Publication US20020025994 A1.

The composition of the present invention includes crosslinked polymeric nanoparticles (PNPs). Typically, the PNPs contain at least 1% by weight, based on the weight of the PNPs, of at least one polymerized multi-ethylenically-unsaturated monomer. Up to and including 99.5% polymerized multi-ethylenically-unsaturated monomer, based on the weight of the PNPs, are capable of being effectively used in the PNPs of the present invention. It is preferred that the amount of polymerized multi-ethylenically-unsaturated monomer is from 1% to 80% based on the weight of the PNPs, more preferably from about 1% to about 60% based on the weight of the PNPs, and most preferably from about 1% to about 25% based on the weight of the PNPs.

Suitable multi-ethylenically-unsaturated monomers useful in the present invention include di-, tri-, tetra-, or higher multifunctional ethylenically unsaturated monomers such as, for example, divinyl benzene, trivinylbenzene, divinyltoluene, divinylpyridine, divinylnaphthalene divinylxylene, ethyleneglycol diacrylate, trimethylolpropane triacrylate, diethyleneglycol divinyl ether, trivinylcyclohexane, allyl methacrylate, ethyleneglycol dimethacrylate, diethyleneglycol di(meth)acrylate, propyleneglycol di(meth)acrylate, trimethylolpropane tri(meth)acrylate, 2,2-dimethylpropane-1,3-diacrylate, 1,3-butylene glycol di(meth)acrylate, 1,4-butanediol diacrylate, 1,6-hexanediol di(meth)acrylate, tripropylene glycol diacrylate, triethylene glycol dimethacrylate, polyethylene glycol 200 diacrylate, tetraethylene glycol di(meth)acrylate, polyethylene glycol dimethacrylate, ethoxylated bisphenol A di(meth)acrylate, polyethylene glycol 600 dimethacrylate, poly(butanediol) diacrylate, pentaerythritol triacrylate, trimethylolpropane triethoxy triacrylate, glyceryl propoxy triacrylate, pentaerythritol tetra(meth)acrylate, dipentaerythritol monohydroxypentaacrylate, divinyl silane, trivinyl silane, dimethyl divinyl silane, divinyl methyl silane, methyl trivinyl silane, diphenyl divinyl silane, divinyl phenyl silane, trivinyl phenyl silane, divinyl methyl phenyl silane, tetravinyl silane, dimethyl vinyl disiloxane, poly(methyl vinyl siloxane), poly(vinyl hydro siloxane), poly(phenyl vinyl siloxane), and mixtures thereof. The term "(meth)acrylic" includes both acrylic and methacrylic and the term "(meth)acrylate" includes both acrylate and methacrylate. Likewise, the term "(meth)acrylamide" refers to both acrylamide and methacrylamide. "Alkyl" includes straight chain, branched and cyclic alkyl groups.

Suitable ethylenically-unsaturated monomers capable of being incorporated as copolymerized units in the PNP include, but are not limited to: (meth)acrylic acid, (meth)acrylamides, alkyl(meth)acrylates, alkenyl(meth)acrylates, aromatic(meth)acrylates, vinyl aromatic monomers, phosphorus-containing compounds such as phosphoethyl(meth)acrylate ("PEM"), vinyl acetates, nitrogen-containing compounds, maleate, mono- and dialkyl esters, maleic acid, maleic anhydride, fumarates, maleamates and their copolymers with vinylaromatics, vinyl ethers, vinyl sulfides, and substituted ethylene monomers. The PNPs useful as dispersants may also contain optional functional monomers including, but not limited to, such functionalities as hydroxyl, acetoacetate, acrylamides, acrylamide/formaldehyde adducts, ureido, amine, siloxane, silane, aminosilane and the like.

Typically, the alkyl(meth)acrylates useful in the present invention are ($C_1$-$C_{26}$)alkyl(meth)acrylates. Suitable alkyl (meth)acrylates include, but are not limited to: acrylic and methacrylic acid esters of straight-chain or branched monoalcohols having 1 to 24 carbon atoms. Useful alkyl (meth)acrylates having 1-22 carbons in the alkyl group include, for example, methyl acrylate, ethyl acrylate, propyl acrylate, isopropyl acrylate, butyl acrylate, pentyl acrylate, hexyl acrylate, 2-ethyl hexyl acrylate, nonyl acrylate, lauryl acrylate, methyl methacrylate, ethyl methacrylate, propyl methacrylate, isopropyl methacrylate, butyl methacrylate, pentyl methacrylate, hexyl methacrylate, 2-ethyl hexyl methacrylate, nonyl methacrylate, lauryl methacrylate, behenyl methacrylate and the like can be used. Useful cycloaliphatic(meth)acrylates include, for example, trimethylcyclohexyl acrylate, t-butyl cyclohexyl acrylate, cyclohexyl methacrylate, isobornyl methacrylate and the like. Useful aryl(meth)acrylates include, for example, benzyl acrylate and benzyl methacrylate.

The alkyl(meth)acrylate monomers useful in the present invention are alternatively a single monomer or a mixture having different numbers of carbon atoms in the alkyl portion. Also, the (meth)acrylamide and alkyl(meth)acrylate monomers useful in the present invention are optionally substituted. Suitable optionally substituted (meth)acrylamide and alkyl(meth)acrylate monomers include, but are not limited to: hydroxy ($C_2$-$C_6$)alkyl(meth)acrylates, dialkylamino($C_2$-$C_6$)-alkyl(meth)acrylates, dialkylamino($C_2$-$C_6$) alkyl(meth)acrylamides.

Useful substituted alkyl (meth)acrylate monomers are those with one or more hydroxyl groups in the alkyl radical, for example, those where the hydroxyl group is found at the β-position (2-position) in the alkyl radical. Hydroxyalkyl (meth)acrylate monomers in which the substituted alkyl group is a ($C_2$-$C_6$)alkyl, branched or unbranched, are preferred. Suitable hydroxyalkyl(meth)acrylate monomers include, but are not limited to: 2-hydroxyethyl methacrylate ("HEMA"), 2-hydroxyethyl acrylate ("HEA"), 2-hydroxypropyl methacrylate, 1-methyl-2-hydroxyethyl methacrylate, 2-hydroxy-propyl acrylate, 1-methyl-2-hydroxyethyl acrylate, 2-hydroxybutyl methacrylate, 2-hydroxybutyl acrylate and mixtures thereof. The preferred hydroxyalkyl (meth)acrylate monomers are HEMA, 1-methyl-2-hydroxyethyl methacrylate, 2-hydroxypropyl methacrylate and mixtures thereof. A mixture of the latter two monomers is commonly referred to as "hydroxypropyl methacrylate" or "HPMA." Polyethylene glycol acrylates and methacrylates, and hydrophobically terminated polyethylene glycol acrylates and methacrylates are useful in the present invention. Preferred polyethylene glycol methacrylate monomers include, but are not limited to HO($CH_2CH_2O$)$_3$-methacrylate (3PEGMA).

Other substituted (meth)acrylate and (meth)acrylamide monomers useful in the present invention are those with a dialkylamino group or dialkylaminoalkyl group in the alkyl radical. Examples of such substituted (meth)acrylates and (meth)acrylamides include, but are not limited to: dimethylaminoethyl methacrylate, dimethylaminoethyl acrylate, N,N-dimethylaminoethyl methacrylamide, N,N-dimethylaminopropyl methacrylamide, N,N-dimethylaminobutyl methacrylamide, N,N-di-ethylaminoethyl methacrylamide, N,N-diethylaminopropyl methacrylamide, N,N-diethylaminobutyl methacrylamide, N-(1,1-dimethyl-3-oxobutyl)acrylamide, N-(1,3-diphenyl-1-ethyl-3-oxobutyl)acrylamide, N-(1-methyl-1-phenyl-3-oxobutyl)methacrylamide, and 2-hydroxyethyl acrylamide, N-methacrylamide of aminoethylethyleneurea, N-methacryloxyethyl morpholine, N-maleimide of dimethylaminopropylamine, and mixtures thereof.

Other substituted (meth)acrylate monomers useful in the present invention are silicon-containing monomers such as γ-propyl tri($C_1$-$C_6$)alkoxysilyl(meth)acrylate, γ-propyl tri ($C_1$-$C_6$)alkylsilyl(meth)acrylate, γ-propyl di($C_1$-$C_6$)alkoxy ($C_1$-$C_6$)alkylsilyl(meth)acrylate, γ-propyl di($C_1$-$C_6$)alkyl ($C_1$-$C_6$)alkoxysilyl(meth)acrylate, vinyl tri($C_1$-$C_6$) alkoxysilyl(meth)acrylate, vinyl di($C_1$-$C_6$)alkoxy($C_1$-$C_6$) alkylsilyl(meth)acrylate, vinyl($C_1$-$C_6$)alkoxydi($C_1$-$C_6$) alkylsilyl(meth)acrylate, vinyl tri($C_1$-$C_6$)alkylsilyl(meth) acrylate, and mixtures thereof.

The vinylaromatic monomers useful as unsaturated monomers in the present invention include, but are not limited to: styrene ("STY"), α-methylstyrene, vinyltoluene, p-methylstyrene, ethylvinylbenzene, vinylnaphthalene, vinylxylenes, and mixtures thereof. The vinylaromatic monomers also include their corresponding substituted counterparts, such as halogenated derivatives, i.e., containing one or more halogen groups, such as fluorine, chlorine or bromine; and nitro, cyano, ($C_1$-$C_{10}$)alkoxy, halo($C_1$-$C_{10}$) alkyl, ($C_1$-$C_{10}$)alkoxy, carboxy, amino, ($C_1$-$C_{10}$)alkylamino derivatives and the like.

The nitrogen-containing compounds useful as unsaturated monomers in the present invention include, but are not limited to: vinylpyridines such as 2-vinylpyridine or 4-vinylpyridine; lower alkyl ($C_1$-$C_8$) substituted N-vinylpyridines such as 2-methyl-5-vinylpyridine, 2-ethyl-5-vinylpyridine, 3-methyl-5-vinylpyridine, 2,3-dimethyl-5-vinylpyridine, and 2-methyl-3-ethyl-5-vinylpyridine; methyl-substituted quinolines and isoquinolines; N-vinylcaprolactam; N-vinylbutyrolactam; N-vinylpyrrolidone; vinyl imidazole; N-vinylcarbazole; N-vinylsuccinimide; (meth) acrylonitrile; o-, m-, or p-aminostyrene; maleimide; N-vinyl-oxazolidone; N,N-dimethylaminoethylvinylether; ethyl-2-cyanoacrylate; vinylacetonitrile; N-vinylphthalimide; N-vinylpyrrolidones such as N-vinylthiopyrrolidone, 3 methyl-1-vinylpyrrolidone, 4-methyl-1-vinylpyrrolidone, 5-methyl-1-vinylpyrrolidone, 3-ethyl-1-vinylpyrrolidone, 3-butyl-1-vinylpyrrolidone, 3,3-dimethyl-1-vinylpyrrolidone, 4,5-dimethyl-1-vinylpyrrolidone, 5,5-dimethyl-1-vinylpyrrolidone, 3,3,5-trimethyl-1-vinylpyrrolidone, 4-ethyl-1-vinylpyrrolidone, 5-methyl-5-ethyl-1-vinylpyrrolidone and 3,4,5-trimethyl-1-vinylpyrrolidone; vinylpyrroles; vinylanilines; and vinylpiperidines.

The substituted ethylene monomers useful as unsaturated monomers in the present invention include, but are not limited to: allylic monomers, vinyl acetate, vinyl formamide, vinyl chloride, vinylbenzyl chloride ("VBC"), vinyl fluoride, vinyl bromide, vinylidene chloride, vinylidene fluoride and vinylidene bromide.

Various substituted vinyl monomers and functionalized vinyl monomers, which are useful for incorporating into PNPs for attaching various dye molecules, are also provided in U.S. Patent Application Publication US20020025994 A1.

A suitable process to prepare the PNPs according to the present invention is free radical solution polymerization of at least one multiethylenically unsaturated monomer, and optionally, at least one second monomer. By "solution polymerization" herein is meant free radical addition polymerization in a suitable solvent for the polymer. By "suitable solvent for the polymer" herein is meant that linear random (co)-polymers having substantially similar polymerized monomer units to the PNPs are soluble in the solvent. Another method for selecting a suitable solvent or mixture of solvents is on the basis of using solubility parameter analysis. According to such methods, the suitability of the solvent is determined by substantially matching the solubility parameters of the PNP and of the solvent, such as the Van Krevelen parameters of delta d, delta p, delta h and delta v. See, for example, Van Krevelen et al., *Properties of Polymers, Their Estimation and Correlation with Chemical Structure*, Elsevier Scientific Publishing Co., 1976; Olabisi et al., *Polymer-Polymer Miscibility*, Academic Press, NY, 1979; Coleman et al., *Specific Interactions and the Miscibility of Polymer Blends*, Technomic, 1991; and A. F. M. Barton, *CRC Handbook of Solubility Parameters and Other Cohesion Parameters*, 2nd Ed., CRC Press, 1991. Delta d is a measure of dispersive interactions, delta p is a measure of polar interactions, delta h is a measure of hydrogen bonding interactions, and delta v is a measure of both dispersive and polar interactions. Such solubility parameters are either calculated, such as by the group contribution method, or determined experimentally, as is known in the art. A preferred solvent has a delta v parameter within 4 (joule per cubic centimeter)$^{1/2}$, preferably within 1 (joule per cubic centimeter)$^{1/2}$ of the polymer delta v parameter. Suitable solvents for the polymerization include organic solvents such as hydrocarbons; alkanes; halohydrocarbons; chlorinated, fluorinated, and brominated hydrocarbons; aromatic hydrocarbons; ethers; ketones; esters; alcohols; and mixtures thereof. Particularly suitable solvents, depending on the composition of the PNP, include dodecane, mesitylene, xylenes, diphenyl ether, gamma-butyrolactone, ethyl acetate, ethyl lactate, propyleneglycol monomethyl ether acetate, caprolactone, 2-heptanone, methylisobutyl ketone, acetone, methyl ethyl ketone, diisobutylketone, propyleneglycol monomethyl ether, and alkyl-alcohols, such as isopropanol, decanol, and t-butanol, and supercritical carbon dioxide.

The PNPs are prepared by first charging a solvent or, alternatively, a mixture of solvent and some portion of the monomers, to a reaction vessel. The monomer charge is typically composed of monomers, initiator, and chain transfer agent, if any. Typically, initiation temperatures are in the range of from 55° C. to about 125° C., although lower or higher initiation temperatures are possible using suitable low temperature or high temperature initiators known in the art. After the heel charge has reached a temperature sufficient to initiate polymerization, the monomer charge or balance of the monomer charge is added to the reaction vessel. The monomer charge time period is typically in the range of from 15 minutes to 4 hours, although both shorter and longer time periods are envisioned. During the monomer charge, the reaction temperature is typically kept constant, although it is possible to vary the reaction temperature. After completing the monomer mixture addition, additional initiator in solvent can be charged to the reaction and/or the reaction mixture may be held for a time.

The PNPs are dispersed in the polymerization solvent or alternatively, they are isolated, for example, by vacuum evaporation, by precipitation into a non-solvent, and by spray drying. The isolated PNPs are subsequently redispersed in a medium appropriate for incorporation into a dispersion or ink composition.

Initiators useful in the free radical polymerization of the PNPs of the present invention include, but are not limited to, one or more of: peroxyesters, dialkylperoxides, alkylhydroperoxides, persulfates, azoinitiators, redox initiators and the like. The amount of the free radical initiator used is typically from 0.05 to 10% by weight, based on the weight of total monomer.

Chain transfer reagents are optionally used to control the extent of polymerization of the PNPs useful in the present invention. Suitable chain transfer agents include, but are not limited to: alkyl mercaptans such as n-dodecyl mercaptan, 3-mercapto propionic acid, trimethylolpropane tri(3-mercaptopropionate) and aromatic hydrocarbons with activated hydrogens such as toluene, and alkyl halides such as bromotrichloromethane.

The PNPs of the present invention contain at least 2.0 wt % of a polarizable group, based on the weight percent of the corresponding monomer or oligomer containing the polarizable group. By "polarizable group" is meant herein a functional group having dipole moment of greater than 1.10 Debye units ($3.67 \times 10^{-30}$ C m). Dipole moments of molecules are determinable by consulting references such as *CRC Handbook of Chemistry and Physics,* 83rd Edition, David Lide editor, CRC Press, 2002, p 9.45 to 9.51.CRC Handbook reference.

The medium of use of the colorant composition containing the PNPs is alternatively water-based, solvent based, or non-aqueous. By "non-aqueous" is meant herein a medium that contains from zero to less than 50 weight % water, based on the weight of the non-aqueous medium. In any of these mediums of use, the polarizable group is an ionizable or nonionic polarizable group. Specifically, the at least 2.0 wt % of a polarizable group is alternatively preferably at least 2 wt %, and more preferably at least 5 wt % of an ionizable polarizable group, and preferably at least 10 wt %, and more preferably at least 20 wt % of a nonionic polarizable group, or a mixture of such groups. By "ionizable group" is meant herein a group which is capable of forming an ionic group in the medium of use or in water. The ionic group may be an anionic group or a cationic group, and the ionizable group may form an anion or a cation. Suitable nonionic polarizable groups include, for example hydroxyalkyl(meth)acrylates, poly(alkylene oxide)esters of methacrylic acid, acrylamides and methacrylamides.

Ionizable functional groups capable of forming anions include, for example, acidic groups, or salts thereof. Such ionizable groups suitable for the present invention include, for example —COOH, —SO$_3$ H and —PO$_3$ H$_2$, —SO$_2$ NHCOR, and their salts, for example —COONa, —COOK, —COO$^-$ NR$_4^+$, —SO$_3$ Na, —HPO$_3$ Na, —SO$_3^-$ NR$_4^+$, and PO$_3$ Na$_2$, where R is a saturated or unsaturated alkyl or phenyl group. Preferred ionizable groups are —COOH, —SO$_3$H and their ammonium, sodium, potassium and lithium salts.

The ionizable group is attached to an organic group that is incorporated into the PNP, such as, for example, by polymerization. The organic group is a substituted or unsubstituted sulfophenyl group or a salt thereof, a substituted or unsubstituted (polysulfo)phenyl group or a salt thereof, a substituted or unsubstituted sulfonaphthyl group or a salt thereof, or a substituted or unsubstituted (polysulfo)naphthyl group or a salt thereof. Organic groups suitable for the present invention include, for example, olefin, hydroxysulfophenyl, p-sulfophenyl and 4-hydroxy-3-sulfophenyl. Preferably, the organic group containing the ionizable group capable of forming an anion has a) an aromatic group or a $C_1$-$C_{24}$ alkyl group and b) at least one of the following: at least one acidic group, at least one salt of an acidic group, or mixtures thereof. Preferably, the pKa of the acidic group or the salt of the acidic group is less than 11, more preferably less than 10, and most preferably less than 9, where "pKa" refers not only to the acidic or acidic salt substituent of the organic group, but to the pKa of the organic group as a whole. In one embodiment of the invention, the aromatic group is further substituted or unsubstituted, for example, with alkyl groups. In the preferred embodiment of the invention, the acidic group is a sulfonic acid group, a sulfinic acid group, a phosphonic acid group, or a carboxylic acid group. In the preferred embodiment of the invention, the organic group containing the ionizable group is an acrylic, phenyl or a naphthyl group. Naphthyl groups suitable for the present invention include naphthyl groups mono-substituted with an acidic group on either ring, or naphthyl groups substituted with more than one acidic group, with the acidic groups on the same or different rings.

After an anionic PNP is formed, and prior to, or while adding it to water to form a dispersion, it's ionizable groups are optionally partially or completely neutralized with an amine or an inorganic base such as ammonium hydroxide or sodium hydroxide. Suitable amines include, for example, AMP (2-amino-2-methyl-1-propanol), dimethyl-AMP, amino methyl propanol, amino ethyl propanol, dimethyl ethanol amine, triethylamine and the like. Where the PNP is to be used in a non-aqueous based or water based application, the ionizable groups are alternatively partially neutralized or left un-neutralized.

Ionizable functional groups capable of forming cations include, for example, amines, quaternary ammonium groups (—NR$_3$$^+$), and quaternary phosphonium groups (—PR$_3$$^+$). In one embodiment of the invention, the amines are protonated to form ammonium groups in acidic media. Preferably, an organic group having an amine substituent has a pKb of less than 5. The ionizable groups can be attached to the same organic groups as those discussed above for the ionizable groups capable of forming anions. Preferably, the organic group contains a) an aromatic group such as a phenyl or a naphthyl group and b) a quaternary ammonium, quaternary phosphonium. Quaternized cyclic amines, and quaternized aromatic amines can also be used as the organic group, including N-substituted pyridinium compounds, such as N-methyl-pyridyl. Organic groups suitable for the present invention include, for example 3-$C_5H_4$N($C_2H_5$)$^+$X$^-$, $C_6H_4$N$C_5H_5$$^+$X$^-$, $C_6H_4$COCH$_2$N(CH$_3$)$_3$$^+$X$^-$, $C_6H_4$COCH$_2$(NC$_5H_5$)$^+$X$^-$, 3-$C_5H_4$N(CH$_3$)$^+$X$^-$, $C_6H_4$N(CH$_3$)$_3$$^+$X$^-$, and $C_6H_4$CH$_2$N(CH$_3$)$_3$$^+$X$^-$, wherein X$^-$ is a halide or an anion derived from a mineral or organic acid. Other examples include p$C_6H_4$—SO$_3$$^-$Na$^+$, p$C_6H_4$—CO$_2$$^-$Na$^+$, and $C_5H_4$N$^+$$C_6H_5$(NO$_3$)$^-$. Optionally, the ionizable groups may partially neutralized, or left un-neutralized, for example where the cationic PNP is intended for use in non-aqueous based or water based applications.

Additional optional functional groups that may be present on the organic group include, but are not limited to, R, OR, COR, COOR, OCOR, halogen, CN, NR$_2$, SO$_2$NR(COR), SO$_2$NR$_2$, NR(COR), CONR$_2$, NO$_2$, SO$_3$M, SO$_3$NR$_4$, and N—NR'. By 'R' is meant herein hydrogen, $C_1$-$C_{24}$ substituted or unsubstituted alkyl (branched or unbranched), $C_3$-$C_{24}$ substituted or unsubstituted alkenyl, ($C_2$-$C_4$ alkyleneoxy)$_x$R", or a substituted or unsubstituted aryl. By 'R"' is meant herein hydrogen, $C_1$-$C_{24}$ substituted or unsubstituted alkyl (branched or unbranched), or a substituted or unsubstituted aryl. By 'R"' is meant herein hydrogen, $C_1$-$C_{24}$ substituted or unsubstituted alkyl, $C_3$-$C_{24}$ substituted or unsubstituted alkenyl, $C_1$-$C_{24}$ substituted or unsubstituted alkanoyl, or a substituted or unsubstituted aroyl. By 'M' is meant herein H, Li, Na, Cs, K, ½ Ca, ½ Zn, ⅓ Zr, or ½ Mg.

In one embodiment of the invention, the organic group is an aromatic group of the formula A$_y$Ar—, which corresponds to a primary amine of the formula A$_y$ArNH$_2$. By 'Ar' is meant herein an aromatic radical such as, for example, phenyl, naphthyl, anthracenyl, phenanthrenyl, biphenyl, pyridinyl, and triazinyl. By 'A' is meant herein a substituent on the aromatic radical independently selected from a functional group described above, or a linear, branched or cyclic hydrocarbon radical (preferably containing 1 to 24 carbons), unsubstituted or substituted with one or more of those functional groups. By 'y' is meant herein an integer from 1 to 5 when 'Ar' is phenyl, an integer from 1 to 7 when 'Ar' is naphthyl; an integer from 1 to 9 when 'Ar' is anthracenyl, phenanthrenyl, or biphenyl; an integer from 1 to 4 when 'Ar' is pyridinyl; or an integer from 1 to 2 when 'Ar' is triazinyl. When 'A' is a ($C_2$-$C_4$ alkyleneoxy)$_x$R" group, it is preferably a polyethoxylate group, a polypropoxylate group, or a random or block mixture of the two.

In one embodiment of the invention, the PNPs are post-functionalized using techniques known in the art for post-functionalizing polymeric materials. Post-polymerization functionalization of the PNPs can be advantageous in that it can be used for to attaching chromophores when preparing colorants, for attaching to pigments when preparing dispersants and colorants, and for compatibilizing the PNPs with dispersion compositions. Thus, colorants containing post-functionalized PNPs have improved dispersancy in various colorant dispersions, for example, paints, plastics, inks and coatings.

The PNPs of the present invention typically have an apparent weight average molecular weight, as determined by GPC, in the range of from 4,000 to 2,000,000, preferably in the range of from 4,500 to 1,000,000, more preferably in the range of from 5,000 to 800,000, even more preferably in the range of from 6,000 to 700,000, even further preferably from 6,500 to 600,000, even more further preferably from 7,000 to 500,000, and most preferably in the range of from 8,000 to 400,000. As used herein, the term "apparent weight average molecular weight" is reflects the size of the PNP particles using standard gel permeation chromatography methods, for example, using THF solvent at 40° C., 3 Plgel Columns (manufactured by Polymer Labs, Amherst, Mass.), 100 Angstroms (10 nm), 10$^3$ Angstroms (100 nm), 10$^4$ Angstroms (1 micron), 30 cm long, 7.8 mm ID, 1 milliliter/minute, 100 microliter injection volume, calibrated to narrow polystyrene standards using Polymer Labs CALIBRE™ software.

Control of PNP particle size and distribution is achieved by one or more of such methods as choice of solvent, choice of initiator, total solids level, amount and type of multifunctional monomer, type and amount of chain transfer agent, initiator level and reaction conditions. In the various embodiments of the present invention, unless indicated otherwise, the PNPs have a mean diameter in the range of from 1 to 50 nm, preferably in the range of from 1 to 40 nm, more preferably in the range of from 1 to 30 nm, even more preferably in the range of from 1 to 25 nm, further preferably in the range of from 1 to 20 nm, and most preferably in the range of from 2 to 10 nm. It is further typical that the PNPs have a mean particle diameter of at least 1.5 nm, preferably at least 2 nm. One method of determining the particle sizes (mean particle diameter) of the PNPs is by using standard dynamic light scattering techniques wherein the correlation functions are converted to hydrodynamic sizes using LaPlace inversion methods, such as CONTIN.

Typically, PNPs including as polymerized units, less than 10 wt % multiethylenically unsaturated monomer, have a glass transition temperature from −90° C. to 170° C. for the composition in the absence of the polymerized multiethylenically unsaturated monomer, as determined by a modulated differential scanning calorimetry measurement. PNPs containing as polymerized units, at least 50 weight % multiethylenically unsaturated monomer are considered to have glass transition temperatures of at least 50° C.

The PNPs are optionally characterized as having suitable hydrophilicities that allow the PNPs to be dispersed into an aqueous medium. One method to characterize the hydrophilicity of the PNPs is to calculate the Hansch parameter. The Hansch parameter is calculated using a group contribution method. The monomer units forming the polymer are assigned a hydrophobicity contribution and the relative hydrophobicity of the polymer is calculated based on the weight average of the monomers in the polymer. Hansch and Fujita, J. Amer. Chem. Soc., 86, 1616-1626 (1964); H. Kubinyi, *Methods and Principles of Medicinal Chemistry*, Volume 1, R. Mannhold et al., Eds., VCH, Weinheim (1993); C. Hansch and A. Leo, *Substituent Constants for Correlation Analysis in Chemistry and Biology*, Wiley, New York (1979); and C. Hansch, P. Maloney, T. Fujita, and R. Muir, Nature, 194. 178-180 (1962). Values of the hydrophobicity contributions for several monomers are listed in Table 1.

TABLE 1

| Monomer | Hydrophobicity Contribution |
| --- | --- |
| ethyl acrylate | 2.11 |
| butyl acrylate | 3.19 |
| 2-ethyl hexylacrylate | 5.22 |
| styrene | 4.29 |
| methyl methacrylate | 1.89 |
| ethyl methacrylate | 2.43 |
| butyl methacrylate | 3.51 |
| isobornyl methacrylate | 2.22 |
| butadiene | 4.0 |
| acrylic acid | −2.52 |
| methacrylic acid | −2.2 |
| maleic anhydride | −3.5 |

Preferred PNPs have a Hansch parameter in the range of from −1 to 4.

The dispersion of the present invention includes particles and PNPs, both of which are dispersed in a liquid medium. By "dispersion" is meant herein a physical state of matter that includes at least two distinct phases, wherein a first phase is distributed in a second phase, the second phase being a continuous medium. The liquid medium is alternatively, at least one organic solvent, water, or mixtures thereof.

The PNPs of the present invention are useful for preparing any type of particle dispersion. One embodiment of the present invention is a dispersion containing particles and PNPs, the PNPs having an acid value of from 0 to 700 (mg KOH/g PNP solids), preferably from 1 to 500 (mg KOH/g PNP solids) and more preferably from 2 to 220 (mg KOH/g PNP solids); an amine value of from 0 to 250, and an hydroxyl number of from 0 to 250 (mg KOH/g PNP solids). Where the particle dispersion is a colorant dispersion, the PVC of the dispersion is alternatively very low (e.g., 1 percent) or quite high (e.g., 99.9 percent). PVC values are typically up to 99.9 percent, more typically up to 99 percent, even more typically up to 98 percent, and most typically up to 97 percent. The colorant dispersions include a liquid medium, such as at least one organic solvent, water, or mixtures of an organic solvent and water. Preferably, the liquid medium is compatible with the PNPs.

The PNPs of the present invention are desirably dispersible, miscible, or otherwise substantially compatible with/in the dispersions or inks in the fluid state or in the dried state. The region or surface of the PNPs that is directed toward the surface of a pigment, a dye, a latex, a substrate, an air interface, a coacervate surface, or an interfacial surface, is not necessarily compatible with the aqueous or nonaqueous medium of the colorant, coating, paint, ink, or other composition medium. Thus, the following discussion on compatibility of PNPs refers to compatibility of the region or surface of PNPs directed toward and interacting with the aqueous or nonaqueous medium of the colorant, coating, paint, or ink after the PNPs have adsorbed on the surface of a colorant, a latex, a substrate, an air interface, a coacervate surface, or an interfacial surface.

The compatibility of the PNPs with the balance of the colorant dispersion is determined by a comparable matching of the solubility parameters of the PNPs and the balance of the colorant dispersion, using solubility parameters such as the above-mentioned Van Krevelen parameters of delta d, delta p, delta h and delta v. When the solubility parameters of the PNP surface and dispersion medium or ink composition medium are substantially similar, the compatibility between the PNP surface and the medium is greater, and phase separation and/or aggregation of the PNPs is less likely to occur. It is preferred that the solubility parameters, particularly delta h and delta v, of the PNPs and ink or other composition medium are substantially matched. "Substantially matched" and "substantially similar" solubility parameters are typically provided when the root-mean-square differences of the delta-d, delta-p, and delta-h solubility parameters between the PNPs and the balance of the ink or other composition medium is less than 5, preferably less than 4, and more preferably less than 3 solubility units. It will be appreciated by those skilled in the art that the properties of the PNP also affect the compatibility of that PNP in the dried state.

In one embodiment of the present invention, the PNPs are incorporated into solution or liquid polymer coatings such as solvent based coatings, polymer dissolved in monomer or oligomer coatings, monomer based coatings and oligomer based coatings. The PNPs are incorporated into the coating to disperse and stabilize materials such as pigments, extenders, and functional particles such as aluminum, zinc, copper, bronze, and silver. The PNPs provide reduced viscosity dispersions of particles such as pigments in solvent based, high solids, low VOC solvent based, and 100 percent solids colorants and coatings. PNPs are particularly useful in polyester, alkyd, epoxy, urethane, siloxane, acrylic urethane and acrylic coatings. PNPs confer to solvent based coatings improved dispersion stability, color acceptance and color stability of pigment dispersions and improved chemical stability against oxidation of metallic pigments.

In another embodiment of the present invention, the PNPs are incorporated into solution or liquid polymer colorants such as solvent based colorants, polymer dissolved in monomer or oligomer colorants, monomer based colorants and oligomer based colorants. Optionally, these colorants are preferably incorporated into PNP containing solutions or liquid polymer coatings such as solvent based coatings, polymer dissolved in monomer or oligmer coatings, monomer based coatings and oligomer based coatings. The PNPs provide reduced viscosity dispersions of particles such as pigments in solvent based, high solids, low VOC solvent based and 100 percent solids colorants and colorants.

In yet another embodiment of the present invention, there are provided colorants and dispersions, including colorant dispersions, containing PNPs having, as polymerized units, at least one multi-ethylenically-unsaturated monomer, and at least one block- or graft copolymer having at least one hydrophobic polymer block and at least one hydrophilic polymer block. Preferred hydrophobic blocks have a delta h solubility parameter less than 0.5, preferably less than 0.2, and more preferably less than 0.1. Preferred hydrophobic blocks contain polymerized units of alkyl(meth)acrylate monomers, more preferably BA and MMA monomers. The hydrophilic blocks are different from the hydrophobic blocks. Preferred hydrophilic blocks have a delta h solubility parameter greater than zero (0), preferably greater than 0.1, and more preferably greater than 0.2. Preferred hydrophilic blocks contain polymerized units of alkyl(meth)acrylic acid monomers, more preferably AA and MAA monomers. The block- or graft-copolymer can be blended with the PNPs in a number of ways, including solvent blending, melt blending, and synthesis of either one of the block-copolymer, graft-copolymer, or the PNP, in the presence of the other. The resulting colorant dispersion made with PNP/block copolymer dispersant have improved compatibility with, and provide improved stability to, for example, polyester paints, alkyd paints, hypoxy paints, urethane paints, acrylic urethane paints, acrylic paints, siloxane paints, latex paints, such as for example, acrylic latex paints, whether these paints be solvent borne, water borne, or water reducible.

As described hereinafter, colorants are substances that include a chromophore, such as pigments and dyes. Chromophores can be attached to PNPs through covalent, ionic, and dispersive interactions. In certain embodiments of the present invention, the chromophores are attached to at least a portion of the PNPs. When the chromophores are pigments, the required ratios of PNP to pigment are provided according to the PNP gyre surface area relationship as described hereinbelow. When the chromophores are dyes or other attached chromophore chemical units on the PNPs, it is typical that at least 10%, preferably at least 25%, more preferably at least 50%, even more preferably at least 75% and even more preferably at least 95% of the PNPs have at least one chromophore attached to the PNPs. Higher chromophore-content PNPs are also envisioned whereby the PNPs each contain, on average, more than one attached chromophore. Examples of dyes or other chromophore chemical units that can be attached to polymers, which can also be attached to PNPs, are provided in U.S. Patent Application Publication US20020025994 A1.

In one embodiment of the present invention, an ink is prepared from the colorant dispersion described hereinabove. In another embodiment of the present invention, the PNPs are incorporated into an ink composition by admixing the PNPs or a dispersion of the PNPs with other dissolved or dispersed polymers and/or other ink adjuvants as are well known to those skilled in the art of ink formulation. Certain ink compositions also contain colorants of the present invention. The ink alternatively include an aqueous and a non-aqueous medium. Certain ink compositions also contain conventional ink adjuvants such as, for example, pigments, emulsifiers, monomers, oligomers, polymers, solvents, coalescing agents, buffers, neutralizers, thickeners or rheology modifiers, humectants, UV absorbers, wetting agents, biocides, plasticizers, antifoaming agents, colorants, waxes, and anti-oxidants.

In one embodiment of the present invention, the PNPs are used as dispersants for particles. In another embodiment of the invention, the particles are colorants, typically pigments. Pigments in an aqueous or non-aqueous medium are dispersed or "ground" in the presence of PNPs, and optionally with other ingredients, as desired. About a monolayer (1-2 $mg/m^2$) of the PNP dispersant adsorbs onto pigment surfaces in a virtually irreversible fashion, and is not displaced by dilution or by competitive adsorption of other species such as surfactant. The same is true where multiple layers of PNP are adsorbed onto the primary PNP monolayer. Certain embodiments of a colorant composition utilizing the dispersion of the present invention contain a variety of other optional ingredients, including for example fillers, plasticizers, antioxidants, surfactants, flow control agents, rheology control agents, and thickeners. Applicants have surprisingly discovered that the anchoring of a primary layer of PNPs on a pigment surface leads to additional adsorption of multiple strongly tethered layers of PNP particles. Applicants have unexpectedly discovered that in some cases, more PNPs are adsorbed onto a pigment surface in the presence of species such as surfactants and solution polymers, than when such species are not present.

In one embodiment of the invention, the PNPs are used as dispersants for pigments that are used as dulling agents, such as for example, silica. By "dulling agent" herein is meant a pigment-containing composition that is used to reduce the gloss of an applied composition such as, for example, an architectural coating, an industrial coating, and automotive top coating, a leather top coat and the top coat of a low gloss floor polish. The addition of PNPs to the dulling agent results in increased stability of the dispersed pigment particles, with the formation of pigment—PNP composite particles. The strong adsorption and stabilizing effect provided by PNPs, combined with their polymer particle nature, reduces the formation of air voids during film formation. Better optical clarity and improved mechanical coupling between the pigment surface and the binder composition is provided by the PNPs. The improved optical clarity provides improved jetness. By "jetness" is meant herein film clarity. The improved coupling between pigments and binders provides improved burnish resistance. By "burnish" herein is meant making glossy by or as if by rubbing. Improved jetness and improved burnish resistance are particularly advantageous in the architectural and industrial coating, automotive, graphic arts, and leather industries. In this embodiment, the PNPs are preferably utilized at levels of from 0.1 to 40 wt %, based on the pigment solids. The performance of the PNP dispersant of this embodiment is enhanced by use of silanes, aminosilanes, siloxanes, titanium alcoxide, aluminum alcoxide, zirconium alcoxide, or cationic functionality. In one embodiment of the invention, PNPs contain functional silanes, such as for example, acrylic functional silanes. In another embodiment of the invention, the PNPs are used in combination with aminosilane additives.

Typically, the amount of PNP dispersant required to sufficiently disperse pigments is determined by ensuring that the ratio of the PNP "gyre" surface area to the pigment surface area is greater than 0.3:1, typically at least 0.5:1, more typically at least 1.0:1, and even more typically at least 1.5:1. The PNP "gyre" surface area is akin to the projected surface area of the three-dimensional PNP particle onto a two-dimensional surface. PNP "gyre" and pigment surface areas are calculated by the following equations:

$$PNP \text{ Gyre Surface Area} = \pi(PNP \text{ mean diameter}/2)^2$$

$$\text{Pigment Surface Area} = 4\pi(\text{pigment mean diameter}/2)^2$$

The pigment mean diameter is determined by measuring the surface area of the pigment using BET nitrogen absorption and assuming a spherical pigment particle shape.

The PNPs stabilize a dispersion using both charge and steric mechanisms. Accordingly, the PNPs are used as dispersants for aqueous pigment dispersions; non-aqueous pigment dispersions; dispersions of non-pigment particles, such as dispersions of minerals and clays; and polymer latices. In one embodiment, PNPs are used as dispersants in polymer particle dispersions, for example, dispersions such as polymer latices prepared by emulsion polymerization processes. Ranges for use of PNPs as dispersants in emulsion polymerization are: from 5 to 80, preferably from 10 to 60, and more preferably from 15 to 40 weight percent PNPs based on total weight of the PNPs and the emulsion polymer media. Among suitable emulsion polymer compositions, any emulsion polymer, copolymer, multi-stage copolymer, interpolymer, core-shell polymer, and the like are capable of incorporating the PNP dispersants of the present invention. While any ethylenically unsaturated monomer may be used, it is preferred that the emulsion polymers which incorporate the PNP dispersants are prepared from at least one of (meth)acrylic, vinyl acetate, and vinylaromatic monomers.

The PNPs are bonded strongly to the dispersed pigment surface by van der Waal forces, chemical bonds, or electrostatic forces, or combination of forces, forming a primary layer of PNPs on the pigment surface. In several embodiments of the present invention, there is provided a method for increasing the strength with which the primary PNP layer and subsequent PNP layers are adsorbed on the colorant. In one embodiment of the invention, this is achieved by the addition of PNP coacervation aids to a pigment dispersion, colorant, ink or paint. Preferably, the coacervate aid is added in amounts of from 1 to 50 wt % based on the weight of the PNP. Suitable coacervation aids include, for example, multiphobes disclosed in U.S. Pat. No. 6,337,366. This increased stability results in improved colorant stability, improved colorant acceptance into paints and coatings, improved compatibility of colorants containing PNPs with a wider range of paint and coating compositions, improved storage stability, increased gloss, increased opacity, increased color strength, reduced viscosity drop when colorants containing PNPs are added to waterbased paints, especially those containing associative thickener.

In another embodiment of the invention, further improvements in color stability and compatibility of colorants (including colorants not containing PNPs) are obtained by using PNPs to disperse and stabilize all pigments in a coating color delivery system, including the pigments in the paint and the pigments in the colorants. In the case of an aqueous latex paint, even further improvement is obtained when the latex binder is also dispersed and stabilized with PNP.

In yet another embodiment of the present invention, a method is provided for increasing the strength with which the PNP is adsorbed on the colorant by use of a locking agent. By "locking agent" is meant herein an additional molecule or chemical or physical agent which interacts with the PNPs to reduce their mobility or solubility. Where the locking agent is added to the colorant dispersion, suitable locking agents include, for example, ethylenically-unsaturated monomers such as alkyl(meth)acrylates, including for example, methyl methacrylate and butyl acrylate and ionizable monomers such as for example, acrylic acid and methacrylic acid. Other suitable locking agents include monomers and oligomers curable by UV and other forms of energy cure, including electron beam, and ultrasound. Where the locking agent is incorporated within the PNP particles, suitable locking agent include, for example, amino-acid-PNP functionality, silane-PNP functionality, epoxy-PNP amine-PNP composites, and olefinic-PNP functionality. In one embodiment of the present invention, the locking agent encapsulates the pigment particles having adsorbed upon their surface PNPs. In this embodiment, the locking agent is added to a dispersion of the pigment particles, wherein the pigment particles have PNPs adsorbed upon their surface. After the dispersion has stabilized, an initiator is added, causing in-situ polymerization of the locking agent. The locking agent polymerizes around the pigment particles, thereby encapsulating them.

In yet still another embodiment of the present invention, a method is provided for increasing the strength with which the PNP is adsorbed on the colorant by topological reconstruction of PNP particles while they are held tethered to the colorant or other adsorbed PNP layers. Examples of this topological reconstruction are interpenetration and entanglement of peripheral polymer loops, cycles and branches on adjacent pairs of PNP particles; relaxation and deformation of PNP loops and branches, and globular structures; and construction of PNPs having entropically interlocking functionality such as, for example, hydrophobes attached via polyethylene oxide chains.

The following examples are presented to illustrate further various aspects of the present invention. All percentages of dispersants and surfactants cited in the examples are on a percent solids basis.

EXAMPLE 1

PNP Preparation

Example 1.1

PNP1 (butyl acrylate/methyl methacrylate/acrylic acid/trimethylol propane triacrylate [35/35/20/10 wt. %]) was prepared via solution polymerization. A 5 liter reactor was fitted with a thermocouple, a temperature controller, a purge gas inlet, a water-cooled reflux condenser with purge gas outlet, a stirrer, and a monomer feed line. To a separate vessel was charged 714.3 g of a monomer mixture (A) consisting of 250 g butyl acrylate (BA), 250 g methyl methacrylate (MMA), 142.9 g acrylic acid (AA), 71.4 g trimethyl propane triacrylate (TMPTA), 24.1 grams of a 75% solution of t-amyl peroxypivalate in mineral spirits (Triganox 125-C75) and 178.6 grams of isopropanol (IPrOH). A charge of 2,480.0 grams of IPrOH was added to the reactor. After sweeping the reactor with nitrogen for approximately 30 minutes, heat was applied to bring the reactor charge to 79° C. When the contents of the reactor reached 79° C., a feed of the monomer mixture was added to the reactor uniformly over 120 minutes using feed pumps. At the end of the monomer feed, the batch was held at 79° C. for 30 minutes before adding additional initiator. The batch was then held at 79° C. for an additional 2½ hours. At the end of the final hold, the batch was neutralized with a mixture of 120.4 g of a 28% aqueous solution of NH4OH diluted in 866.0 grams of water. The neutralized polymer solution was transferred to a roto-evaporator and stripped of solvent at ~65° C. under full house vacuum. After removing the solvent the batch was further diluted with additional water to 35.5% polymer in water and final pH is adjusted to ~9.0. Particle size was measured at 5.5 nm.

Example 1.2

PNP2 (butyl acrylate/methyl methacrylate/phosphoethylmethacrylate/acrylic acid/trimethyol propane triacrylate [36/14/20/20/10 wt. %]) was prepared via solution polymerization. A 5 liter reactor was fitted with a thermocouple, a temperature controller, a purge gas inlet, a water-cooled reflux condenser with purge gas outlet, a stirrer, and a monomer feed line. To a separate vessel was charged 480 g of a monomer mixture (A) consisting of 172.8 g butyl acrylate (BA), 67.2 g methyl methacrylate (MMA), 96 g phosphoethylmethacrylate, 96 g acrylic acid (AA), 48 g trimethylol propane triacrylate (TMPTA and), 19.2 grams of a 75% solution of t-amyl peroxypivalate in mineral spirits (Triganox 125-C75) and 120 grams of isopropanol (IPrOH). A charge of 2,480 grams of IPrOH was added to the reactor. After sweeping the reactor with nitrogen for approximately 30 minutes, heat was applied to bring the reactor charge to 79° C. When the contents of the reactor reached 79° C., a feed of the monomer mixture was added to the reactor uniformly over 120 minutes using feed pumps. At the end of the monomer feed, the batch was held at 79° C. for 30 minutes before adding additional initiator. The batch was then held at 79° C. for an additional 2½ hours. At the end of the final hold, the batch was neutralized with a mixture of 161.8 g of a 28% aqueous solution of NH4OH diluted in 480.0 grams of water. The neutralized polymer solution was transferred to a roto-evaporator and stripped of solvent at ~65° C. under full house vacuum. After removing the solvent the batch was further diluted with additional water to 34.7% polymer in water and final pH was adjusted to ~9.0. Particle size was measured at 2.2 nm.

Example 1.3

PNP3 (butyl acrylate/methyl methacrylate/C12/14-EO3-PO3-HNOC(CH3)C═CH2/acrylic acid/methacrylic acid/trimethyol propane triacrylate [29.85/29.85/10/18.6/1.7/10 wt. %]) was prepared via solution polymerization, using the same process described in Example 1.2 above.

Example 1.4

PNP with Poly (Butly Acrylate) Coacervation Aid

PNP4 ((butyl acrylate/methyl methacrylate/acrylic acid/trimethyol propane triacrylate [35/35/20/10 wt. %]) is prepared via solution polymerization. A 12-liter reactor is fitted with a thermocouple, a temperature controller, a purge gas inlet, a water-cooled reflux condenser with purge gas outlet, a stirrer, and a monomer feed line. To a separate vessel is charged 714.3 g of a monomer mixture (A) consisting of 250.0 g butyl acrylate (BA), 250.0 g methyl methacrylate (MMA), 142.9.0 g acrylic acid (AA), 71.4 g trimethylol propane triacrylate (TMPTA), 24.1 grams of a 75% solution of t-amyl peroxypivalate in mineral spirits (Triganox 125-C75) and 178.6 grams of isopropanol (IPrOH). A charge of 2,480.0 grams of IPrOH is added to the reactor. After sweeping the reactor with nitrogen for approximately 30 minutes, heat is applied to bring the reactor charge to 79° C. When the contents of the reactor reaches 79° C., a feed of the monomer mixture is added to the reactor uniformly over 120 minutes using feed pumps. At the end of the monomer feed, the batch is held at 79° C. for 30 minutes before adding additional initiator. The batch is then held at 79° C. for an additional 2½ hours. At the end of the final hold, the batch is neutralized with a mixture of 120.4 g of a 28% aqueous solution of NH4OH diluted in 2538.0 grams of water and the temperature allowed to drop to about 45° C. A mixture of 12.0 grams of a 75% solution of t-amyl peroxypivalate in mineral spirits (Triganox 125-C75), 357.0 grams butyl acrylate and 100.0 grams of isopropanol (IPrOH) is added to the reactor with good stirring. The reactor is again heated to 79° C. and held at this temperature for 3 hours. After cooling to room temperature, approximately 20 grams of 28% aqueous of NH4OH is added to ensure the pH is above 8.5. The neutralized polymer solution is transferred to a roto-evaporator and stripped of solvent at ~65° C. at reduced pressure. After removing the solvent the batch is further diluted with additional water to 30% polymer in water and final pH is adjusted to ~9.0. The particle size is greater than 6.0 nm, but less than about 20 nm. This PNP is modified with 0.5 part poly butyl acrylate per part of PNP (the composite particle is 33.3% p(BA) and 66.7% butyl acrylate/methyl methacrylate/acrylic acid/trimethyol propane triacrylate (35/35/20/10 wt. %). The modified PNP shows enhanced adsorption to pigments and other surfaces.

Example 1.5

PNP with Block Copolymer Coacervation Aid

PNP5 (butyl acrylate/methyl methacrylate/acrylic acid/trimethyol propane triacrylate [35/35/20/10 wt. %]) is prepared via solution polymerization, wherein the process of Example 1.1 is modified to include 142.9 g of the block copolymer Pluronic L31, 100% active (BASF Corp.). This coacervation aid is added in the initial kettle charge or to the reaction mixture after polymerization. The resulting PNP is modified with 20 wt % of the block copolymer and has a particle size greater than 4.0 nm, but less than about 20 nm. The modified PNP shows enhanced adsorption to pigments and other surfaces.

EXAMPLE 2

Pigment Dispersion Preparation and Performance

The composition listed below was loaded into a 100 ml polypropylene screw cap jar. Then 45 g of 1.6 mm glass beads such as A-130 (manufactured by Potters Industries Inc, Berwyn, Pa.) was added, the lid was closed and the jar was inserted into the carrier basket of a Hauschild Flacktek SpeedMixer DAC 150FVZ (manufactured by Hauscild, Germany, US agents FlackTek Inc. Landrum, S.C.). The chamber door was closed and the mixer run for a total of 15 minutes at 2,000 rpm. The particle size was found to be 209 nm. Color acceptance and stability into commercial and model paints was found to be excellent. The pigment dispersion was tested in Sherwin Williams Ever Clean™ Extra White latex paint at 5% w/w. Hand mixing compared to high shear dispersion at 2,000 rpm resulted in CIE 1976 delta E=0.261, and the gloss difference was 0.0% at 60°. Rub up for the pigment dispersion was less than CIE 1976 delta E=0.895.

In a comparative example (Example C2), the PNP was replaced by dispersants known in the prior art. The same procedure was followed, and the colorant was dispersed for the same time and at the same speed. The particle size was found to be 329 nm. Color acceptance and stability into commercial and model paints was found to be less good than that provided by the inventive PNP colorant above. The pigment dispersion was tested in Sherwin Williams Ever Clean™ Extra White latex paint at 5% w/w. Rub up for the pigment dispersion was CIE 1976 delta E=5.246. Hand mixing compared to high shear dispersion at 2,000 rpm resulted in CIE 1976 delta E=0.697, and the gloss difference was +7.1% at 60°.

| Component | Type | Example 2 Mass (g) | Example C2 Mass (g) |
|---|---|---|---|
| Propylene Glycol | Solvent | 7.0 | 5.8 |
| PNP1 | PNP Dispersant | 5.0 | — |
| Morez ™ 101 | Copolymer Dispersant | — | 5.0 |
| Water | Water | 19.3 | 29.8 |
| Tamol ™ SN | Surfactant | — | 0.7 |
| Ammonia 30% | Base | — | 0.9 |
| AVD2227 | Multiphobe | 0.7 | — |
| Raven ™ 14 | Carbon Black | 12.0 | 10.0 |
| Water | Water | 5.0 | 5.0 |
| Particle Size (nm) | | 209 | 329 |
| Hand mixing compared to high shear dispersion: | | | |
| Color acceptance (CIE 1976 delta E) | | 0.261 | 0.697 |
| Gloss difference at 60° | | 0.0% | +7.1% |
| Rub Up (CIE 1976 delta E) | | 0.895 | 5.246 |

Morez ™ 101 is manufactured by Rohm and Haas Company, located in Philadelphia, Pennsylvania.
Tamol ™ SN is manufactured by Rohm and Haas Company, located in Philadelphia, Pennsylvania.
AVD2227 was prepared according to the disclosure of U.S. Pat. No. 6,337,366.
Raven ™ 14 is manufactured by Columbian Chemicals, located in Marietta, GA.

EXAMPLE 3

Preparation and Properties of Paint Containing PNP Dispersant

The ingredients were combined and dispersed according to the usual methods known in the art as follows. The grind stage was added to a 100 mL polypropylene jar, with the second portion of water (10.70 g) held initially. The loaded jar was inserted into a Hauschild Flacktek SpeedMixer DAC 150FVZ. The chamber door was closed and the mixer was run for a total of 3 minutes at 2,200 rpm. The pigment grind was found to be less than 5 microns on a 0-25 micron Hegman gauge. The second portion of water was added and mixed on the SpeedMixer for 30 s at 2,000 rpm. The first four ingredients of the letdown stage were assembled in order, with mixing at about 300 rpm on a benchtop lab mixer with stainless steel propeller type mixer blade in a stainless steel vessel. The grind stage was added to the letdown with stirring. The remaining water was used to wash out containers. The paint was found to have improved gloss, color acceptance, opacity and stability.

In a comparative example (Example C3), the PNP dispersant of Example 3 was replaced by an equal weight of Tamol™ 1124 (manufactured by Rohm and Haas Company, located in Philadelphia, Pa.). The paint was found to have improved gloss 43.7% at 20° compared to 26.3% at 20°, color acceptance CIE 1976 delta E=0.463 compared to delta E=2.025 with 10 wt % Colortrend™ 888 Lamp Black (Creanova Inc., Piscataway, N.J.), reduced viscosity drop with 4 Krebs units less viscosity change after addition of 10 wt % Colortrend™ 888 Lamp Black colorant, and untinted contrast ratio 0.984 compared to 0.980.

| Component | Type | Example 3 Mass (g) | Example C3 Mass (g) | Example 4 Mass (g) |
|---|---|---|---|---|
| Grind | | | | |
| Propylene Glycol | Solvent | 3.34 | 3.34 | 3.34 |
| PNP2 | PNP Dispersant | 3.38 | — | — |
| PNP3 | PNP Dispersant | — | — | 7 |
| Tamol ™ 1124 | Copolymer dispersant | — | 3.38 | — |
| Water | Water | 6.69 | 6.69 | 6.69 |
| BYK-022 | Defoamer | 0.33 | 0.33 | 0.33 |
| Ti-Pure ™ R-706 | Titanium Dioxide | 66.87 | 66.87 | 66.87 |
| Water | Water | 10.70 | 10.70 | 10.7 |
| Grind Sub-total | | 91.32 | 91.32 | 91.32 |
| LetDown | | | | |
| Water | Water | 10.03 | | 10.03 |
| Rhoplex ™ SG-10M | Binder | 152.13 | | 152.13 |
| Texanol ™ | Coalescent | 6.77 | | 6.77 |
| Acrysol ™ RM-8 3% | Thickener | 3.34 | | 3.34 |
| Water | Water | 16.72 | | 16.72 |
| Total | | 280.32 | | 280.32 |
| Property | Value | | | |
| Total PVC | | 20.1% | | 20.1% |
| Volume Solids | | 37.5% | | 37.5% |
| Weight Solids | | 50.7% | | 50.7% |
| Density | | 1.265 kg/L | | 1.265 kg/L |
| Total Dispersant | | 1.0% | | 2.0% |
| Total Coalescent | | 9.0% | | 9.0% |
| VOC | | 125 g/L | | 125 g/L |
| Gloss at 20° | | 4.37% | | 26.3% |
| Color Acceptance (CIE 1976 delta E) | | 0.463 | | 2.025 |
| Untinted contrast ratio | | 0.984 | | 0.98 |

Tamol ™ 1124 (manufactured by Rohm and Haas Company, located in Philadelphia, Pennsylvania).
BYK-022 ™ is manufactured by BYK-Chemie GmbH, located in Wesel, Germany.
Ti-Pure ™ R-706 is manufactured by DuPont Company Titanium Technologies, located in Wilmington, DE.
Rhoplex ™ SG-10Mis manufactured by Rohm and Haas Company, located in Philadelphia, Pennsylvania.
Acrysol ™ RM-8 is manufactured by Rohm and Haas Company, located in Philadelphia, Pennsylvania.

EXAMPLE 4

Preparation and Properties of Paint Containing PNP Dispersant with Entropically Interlocking Functionality A PNP having entropically interlocking functionality was provided. PNP3 was made with 10% hydrophobically modified polyethylene glycol methacrylate monomer. The same process as described in Example 3 above was followed, except the pigment grind stage was warmed to 50° C. and held for 10 minutes with mixing at 1600 rpm after dispersion. The paint was completed in the manner described in Example 2 above. The paint was found to have improved color acceptance of colorants, gloss, opacity, and storage stability, as well as reduced viscosity drop upon the addition of colorant.

EXAMPLE 5

PNP Dispersant Adsorption Properties

The adsorption properties of PNP dispersants PNP1 (Example 5.1), and PNP2 (Example 5.2), were compared to those of Tamol™ 165A (comparative Example C5.3), a commercial dispersant. The pigment dispersions described above were centrifuged at 100,000 rpm for 20 minutes to separate pigment from the continuous phase. The clear supernatant phase was measured to determine solids content as a measure of the polymer concentration. A reference measurement without pigment was made to calibrate the effect of polymer separation under these conditions. Slight reduction of dispersed PNP concentration occurred at the top of the centrifuge sample. The PNP solids was about 2.3% lower than in an uncentrifuged sample. The measured polymer solids was used to determine the quantity of polymer adsorbed on the pigment surface. It was seen that the commercial dispersant adsorbed up to about a maximum of 0.6 mg/m$^2$. Surprisingly, the PNPs did not exhibit any plateau and adsorption occurred beyond a monolayer (about 1-2 mg/m$^2$).

| Wt % polymer on TiO2 | Adsorption (mg/m$^2$) | | |
|---|---|---|---|
| | Example 5.1 PNP1 | Example 5.2 PNP2 | Example C5.3 Tamol™ 165A (Copolymer) |
| 0.1 | 0.023 | 0.11 | 0.016 |
| 0.24 | 0.24 | 0.34 | 0.09 |
| 0.6 | 0.92 | 0.99 | 0.198 |
| 1.2 | 1.97 | 1.95 | 0.39 |
| 4.8 | 6.98 | 7.51 | 0.63 |

Tamol™ 165A (copolymer of diisobutylene and maleic anhydride) is manufactured by Rohm and Haas Company, located in Philadelphia, Pennsylvania.

EXAMPLE 6

PNP Adsorption onto Pigment

Pigment is dispersed with PNP in a xylene solvent in the presence of a solution polymer (Acryloid™ DM55, manufactured by Rohm and Haas Company, located in Philadelphia, Pa.). The PNP is preferentially adsorbed from the mixture of PNP and solution polymer. About a monolayer (1-2 mg/m$^2$) of PNP adsorbs onto the pigment surface in a virtually irreversible fashion, and is not displaced by competitive adsorption of solution polymer. Surprisingly, it is found that more PNP is adsorbed onto a pigment surface in the presence of the solution polymer than is adsorbed absent the surfactant. Similar results are found where the pigment is dispersed in water rather than a solvent.

EXAMPLE 7

Pigment Dispersion Containing PNP, Coacervation Aid, and Locking Agent

A pigment dispersion is prepared with solvent, pigment, and PNPs. A multiphobe coacervation aid is also used. The pigment is dispersed with the application of energy by a disperser blade.

| Component | Type | Example 7 Mass (g) | Example C7 Mass (g) |
|---|---|---|---|
| Water | Water | 15 | 15 |
| PNP2 | PNP Dispersant | 5 | — |
| Morez™ 101 | Copolymer Dispersant | — | 4 |
| Tamol™ 731 | Copolymer Dispersant | — | 1 |
| Ammonia 30% | Base | — | 0.9 |
| Ti-Pure™ R-706 | Titanium Dioxide | 100 | 100 |
| Water | Water | 16.5 | 16.1 |
| | | 137 | 137 |

To the warmed dispersed pigment PNP coacervate composite is then added about 10% of a methyl methacrylate locking agent with mixing. Polymerization is initiated by free radical initiator. Mixing is maintained while polymerization continues. The pigment remains stably dispersed and does not require further milling. The pigment dispersion is then cooled and dried to form a dry powder colorant which redisperses at the point of color delivery.

In a comparative (Example C7), the PNP dispersant is replaced by a copolymer dispersant. The dispersion is found to coagulate and flocculate, and requires further milling to redisperse pigment particles.

EXAMPLE 8

Preparation of Pigment Dispersion Containing PNP and Locking Agent

A pigment dispersion is prepared with solvent, pigment, and PNPs. A multiphobe coacervation aid is also used. The pigment is dispersed with the application of energy by a disperser blade.

| Component | Type | Example 8 Mass (g) |
|---|---|---|
| Water | Water | 15 |
| PNP-epoxy functional | PNP Dispersant | 5 |

-continued

| Component | Type | Example 8 Mass (g) |
|---|---|---|
| Ti-Pure ™ R-706 | Titanium Dioxide | 100 |
| Water | Water | 16.5 |
| | | 137 |

To the warmed dispersed pigment PNP coacervate composite is then added about 2% of a hexamethylene diamine locking agent with mixing. Mixing is maintained while polymerization continues. The pigment dispersion is used in its liquid form, further compounded with additives such as thickeners, other pigment dispersions, polymer emulsions and paints.

EXAMPLE 9

Solvent Based Pigment Dispersion Preparation and Performance

The composition listed below is loaded into a 100 ml polypropylene screw cap jar. Then 45 g of 1.6 mm glass beads such as A-130 (manufactured by Potters Industries Inc, Berwyn, Pa.) is added, the lid is closed and the jar is inserted into the carrier basket of a Hauschild Flacktek SpeedMixer DAC 150FVZ (manufactured by Hauscild, Germany, US agents FlackTek Inc. Landrum, S.C.). The chamber door is closed and the mixer run for a total of 10 minutes at 2,000 rpm. The particle size is found to be 168 nm. Color acceptance and stability into commercial and model paints is found to be excellent.

In a comparative example (Example C9), the PNP is replaced by dispersants known in the prior art. The same procedure is followed, and the colorant is dispersed for the same time and at the same speed. The particle size is found to be 185 nm. Color acceptance and stability into commercial and model paints is found to be inferior to that provided by the inventive PNP colorant above.

| Component | Type | Example 9 Mass (g) | Example C9 Mass (g) |
|---|---|---|---|
| Propylene Glycol Acetate Methyl Ether | Solvent | 13.5 | 13.5 |
| PNP1 | PNP Dispersant | 3.8 | — |
| Solsperse ™ 17000 | Polymeric Dispersant | — | 3.8 |
| Engelhard Zulu Blue 4863 | Copper phthalocyanine 15:2 | 12.0 | 12.0 |
| Propylene Glycol Acetate Methyl Ether | Solvent | 5.0 | 5.0 |
| Particle Size (nm) | | 168 | 185 |

Solsperse ™ 17000 is manufactured by Avecia Chemicals and Additives, Wilmington, DE.

We claim:

1. A colorant composition comprising at least one chromophore, polymeric nanoparticles (PNPs), a locking agent, and 0.01 to 50 wt %, based on the weight of said PNPs, of a PNP coacervation aid;
   wherein said PNPs comprise, as polymerized units, at least one multi-ethylenically unsaturated monomer;
   wherein said PNPs have a mean diameter in the range of from 1 to 50 nanometers, an acid value in the range of from 0 to 700 mg KOH/g PNP solids, an amine value in the range of from 0 to 250, a hydroxyl number in the range of from 0 to 250 mg KOH/g PNP solids, and contain at least 2% of a polarizable group, and
   wherein said colorant composition provides improved colorant stability, improved colorant acceptance into paints and coatings, improved compatibility of colorants with a wider range of paints and coating compositions, improved storage stability, increased color strength, and reduced viscosity drop when added to water-based paints, all relative to colorant compositions absent PNPs and 0.01 to 50 wt %, based on the weight of said PNPs, of a PNP coacervation aid.

2. The composition according to claim 1 wherein said PNPs have a Hansch hydrophobicity parameter value of −1.0 to 4.0.

3. The composition according to claim 1 wherein said locking agent comprises at least one of an alkyl(meth)acrylates, acrylic acid and methacrylic acid, monomers and oligomers curable by UV and other forms of energy cure and ultrasound, and molecule or chemical or physical agent having amino-acid-PNP functionality, silane-PNP functionality, epoxy-PNP amine-PNP composites, or olefinic-PNP functionality.

* * * * *